United States Patent [19]

Takei et al.

[11] Patent Number: 5,392,725
[45] Date of Patent: Feb. 28, 1995

[54] SEWING MACHINE NEEDLE AND METHOD FOR MANUFACTURING SAME

[75] Inventors: Yoshitsugu Takei; Tsutomu Kojima, both of Ueda, Japan

[73] Assignee: Organ Needle Co., Ltd., Nagano, Japan

[21] Appl. No.: 966,145

[22] PCT Filed: May 11, 1992

[86] PCT No.: PCT/JP92/00599

§ 371 Date: Jan. 7, 1993

§ 102(e) Date: Jan. 7, 1993

[87] PCT Pub. No.: WO92/20851

PCT Pub. Date: Nov. 26, 1992

[30] Foreign Application Priority Data

May 10, 1991 [JP] Japan .................. 3-135954

[51] Int. Cl.⁶ .................... D05B 85/00; B21G 1/02
[52] U.S. Cl. ............................ 112/222; 163/5
[58] Field of Search ............. 112/222, 223, 224, 225, 112/226, 227; 163/5, 1, 2, 3, 4; 223/102

[56] References Cited

U.S. PATENT DOCUMENTS

| | | |
|---|---|---|
| 1,949,350 | 2/1934 | Brown . |
| 3,589,428 | 6/1971 | Masujima .................. 163/5 |
| 3,986,468 | 10/1976 | Szostak et al. . |
| 4,037,641 | 7/1977 | Zocher . |
| 4,044,814 | 8/1977 | Zocher . |
| 4,128,067 | 12/1978 | Zocher . |
| 4,458,614 | 7/1984 | Iwashita .................. 112/222 |
| 4,524,815 | 6/1985 | Pavel et al. .................. 163/5 |
| 4,598,753 | 7/1986 | Zylbert . |

FOREIGN PATENT DOCUMENTS

| | | |
|---|---|---|
| 56-37512 | 6/1981 | Japan . |
| 60-134489 | 11/1985 | Japan . |
| 61-29813 | 3/1986 | Japan . |
| 61-40440 | 7/1986 | Japan . |
| 734656 | 8/1955 | United Kingdom . |

*Primary Examiner*—Peter Nerbun
*Attorney, Agent, or Firm*—Price, Gess & Ubell

[57] ABSTRACT

A sewing machine needle is manufactured without producing any burrs on a blade by subjecting the whole blade to die pressing. A needle blank (10) is subject to double swaging, resulting in it being formed with blade sections (14, 16). Then, the needle blank is formed with an elongated portion (22) for subsequently forming a clearance-above-eye above a needle eye. The die pressing permits both side surfaces of a long groove (28) to be spread so as to be spaced from each other at a predetermined angle, and permits the clearance-above-eye (40) and eye portion (33) to be formed. The sewing machine needle thus formed exhibits sufficient rigidity and provides an increased space between the blade and a sewing thread, resulting in a sewing operation being carried out stably and at an increased speed.

20 Claims, 6 Drawing Sheets

5,392,725

SEWING MACHINE NEEDLE AND METHOD FOR MANUFACTURING SAME

TECHNICAL FIELD

This invention relates to a sewing machine needle and a method for manufacturing the same.

BACKGROUND ART

Conventionally, manufacturing of a sewing machine needle has been carried out by a press operation such as die press operation or die pressing, flow press operation, or the like in place of metal cutting or machining. However, such a well-known press operation requires a combination of a punching operation, a grinding operation and an abrading operation, with the result that a plurality of different press dies have to be used and the operation is highly troublesome.

Also, the conventional press operation causes burrs to be produced on a blade of the needle due to the use of dies. Unfortunately, removal of burrs is time- and labor-consuming, therefore, the flow press operation or flow pressing which is said to prevent production of burrs on the blade during formation of the needle has been recently proposed, as disclosed in U.S. Pat. No. 4,044,814.

However, in order to form a metal blank into the blade of the sewing machine needle by flow pressing while preventing formation of burrs on the blade, it is essential that a volume of the metal of the blank flowing into a extraneous cavity formed between a pair of dies be reduced to an amount smaller than that of a volume of the cavity. Also, when the amount of the metal of the blank is very insufficient or the blade is formed with a long groove by coining which causes burrs to be formed on the blade, the strength and quality of the needle is decreased, and loss due to inferior products and manufacturing difficulties increase, leading to an increase in manufacturing costs.

Further, formation of a clearance-above-eye of an insufficient depth on the blade causes a loop of a sewing thread to be often formed into a small size when the thread is fed to the needle while being kept somewhat stretched, so that a looper is apt to fail to satisfactorily catch the loop. Thus, mounting of the sewing machine needle on a sewing machine requires troublesome operations such as adjustments of the sewing machine, including timing adjustment, adjustment of a feed dog or the like, so that handling and operation of the sewing machine require much time and labor.

DISCLOSURE OF INVENTION

The present invention has been made in view of the foregoing disadvantages of the prior art.

Accordingly, it is an object of the present invention to provide a sewing machine needle which is capable of exhibiting high quality while providing sufficient buckling strength and substantially preventing breakage of the needle.

It is another object of the present invention to provide a sewing machine needle which is capable of providing a gap of a large size between a blade and a sewing thread to facilitate the sewing operation and permit a sewing machine to be driven at a high speed.

It is a further object of the present invention to provide a method for manufacturing a sewing machine needle which is capable of readily and inexpensively manufacturing a sewing machine needle which exhibits sufficient strength and ensures a stable sewing operation at a high speed.

In accordance with one aspect of the present invention, a method for manufacturing a sewing machine needle is provided. The method comprises the step of forming a needle blank with a shank of a large diameter and a cylindrical shape, a first blade section of a diameter smaller than the shank contiguous to a distal end of the shank and a second blade section of a diameter smaller than the first blade section contiguous to a distal end of the first blade section, the first and second blade sections constituting the blade; forming the second blade section with an elongated portion corresponding to a clearance-above-eye of the sewing machine needle; and subjecting the blade to die pressing to form a long groove of a recessed shape extending from the shank to a portion of the second blade section in proximity to a needle point and a needle eye portion having a thin eye accommodating web arranged along the continuous groove, and deform the elongated portion to form the clearance-above-eye. The long groove of the blade has inner side surfaces and outer side surfaces spread at a predetermined angle, respectively, by deforming the blade.

Thus, in the method of the present invention, the blade of which the second blade section is previously formed with the elongated portion corresponding to the clearance-above-eye of the finished sewing machine needle is subject to die pressing, so that the clearance-above-eye may be formed into a sufficient depth without producing any burrs on the blade. Thus, in accordance with the method of the present invention, a sewing machine needle provided with sufficient rigidity and having high quality can be manufactured.

In accordance with another aspect of the present invention, a sewing machine needle is provided which includes a cylindrical shank of a large diameter, a blade arranged so as to extend from the shank and a sharp needle point formed at a distal end of the blade, wherein a continuous long groove of a recessed shape is provided so as to extend from the shank to a portion of the blade in proximity to the needle point, a needle eye portion is formed along the long groove and the blade is formed with a clearance-above-eye. The blade is divided into a first blade section and a second blade section through two frust-conical portions formed on the blade in a manner to be spaced from each other, wherein the needle eye portion is arranged at the second blade section. A constriction is arranged contiguous to the second blade section and in proximity to the needle eye portion of the second blade section and formed into a sectional area smaller than the second blade section. The clearance-above-eye is provided on the constriction in a manner to be opposite to the long groove. The blade has inner side surfaces defining the long groove and outer side surfaces, each being spread at a predetermined angle. The constriction, clearance-above-eye, inner side surfaces and outer side surfaces are formed by die pressing.

In the sewing machine needle of the present invention, the blade is subject to double swaging, resulting in it being divided into the first and second blade sections. Also, the constriction including the clearance-above-eye of a sufficient depth is formed above the needle eye, so that the whole needle has increased rigidity and a gap defined between the blade and a sewing thread is increased to tender the sewing operation stable.

BEST MODES FOR CARRYING OUT INVENTION

Now, the present invention will be described with reference to FIGS. 1 to 10.

Figure 1:
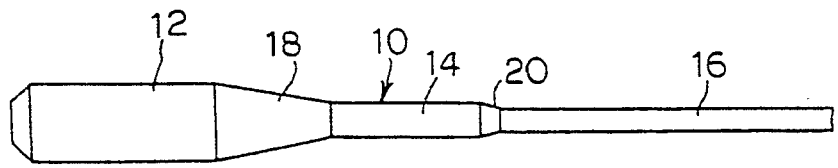
FIG. 1 is a side elevation view showing a needle blank which has been subject to double-swaging suitable for manufacturing a sewing machine needle according to a method of the present invention.

FIG. 1 shows a configuration of a needle blank 10 which has been subject to double-swaging suitable for manufacturing a sewing machine needle according to a method of the present invention. The needle blank 10 thus configured generally includes a cylindrically shaped shank 12 having a large diameter, a first blade section 14 of a cylindrical shape formed with a diameter smaller than the shank 12 and connected at one end thereof through a first frust-conical portion 18 to the shank 12, and a second blade section 16 of a cylindrical shape formed with a diameter smaller than the first blade section 14 and connected at one end thereof through a second frust-conical portion 20 to the other end of the first blade section 14. The first and second blade sections 14 and 16 constitute a blade.

Figure 2:
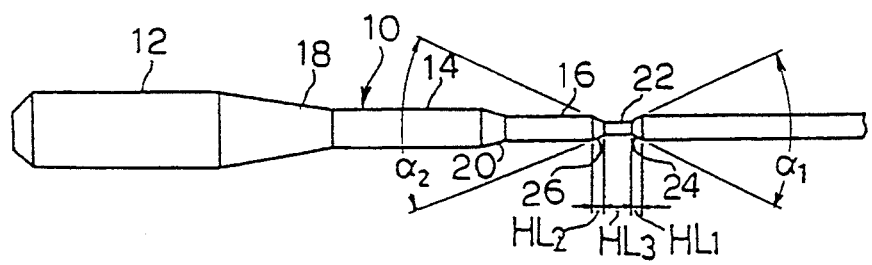
FIG. 2 is a side elevation view of the needle blank which has been further subject to a plastic working to decrease a diameter of a part of a blade of the needle blank.
Figure 3:
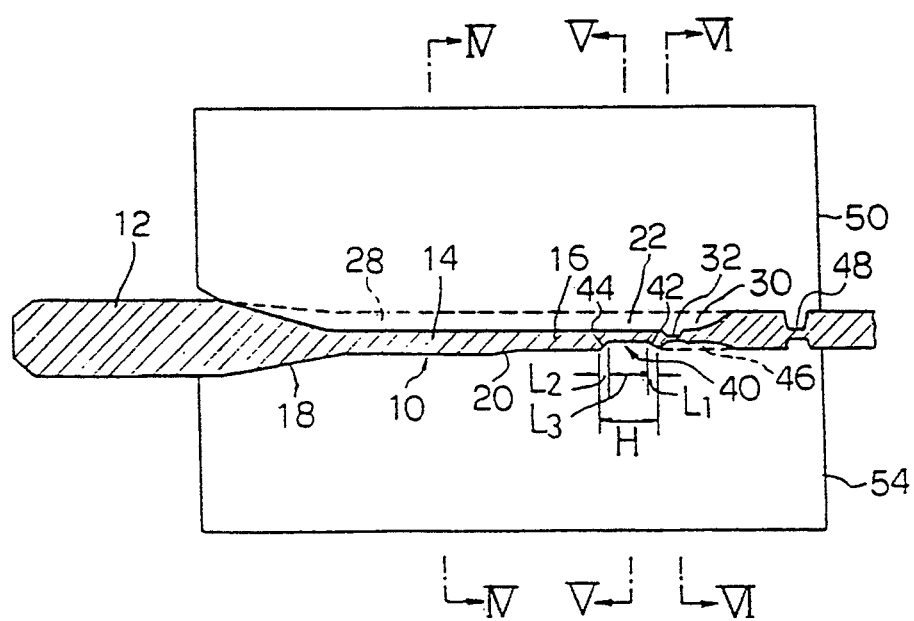
FIG. 3 is a longitudinal sectional view showing the needle blank of FIG. 2 which has been subject to pressing.
Figure 4:
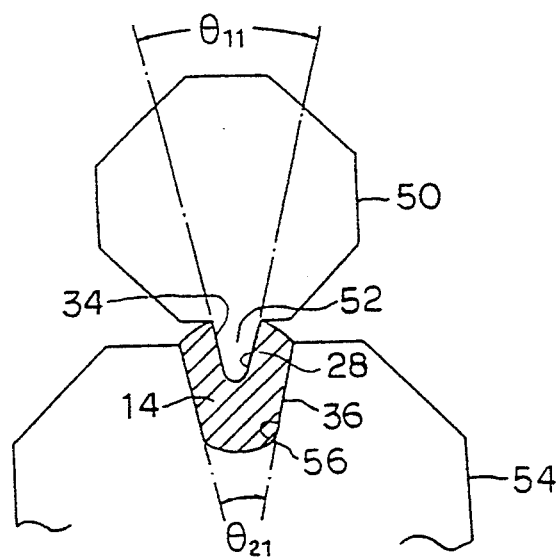
FIG. 4 is a cross-sectional view taken along line IV—IV of FIG. 3.
Figure 5:
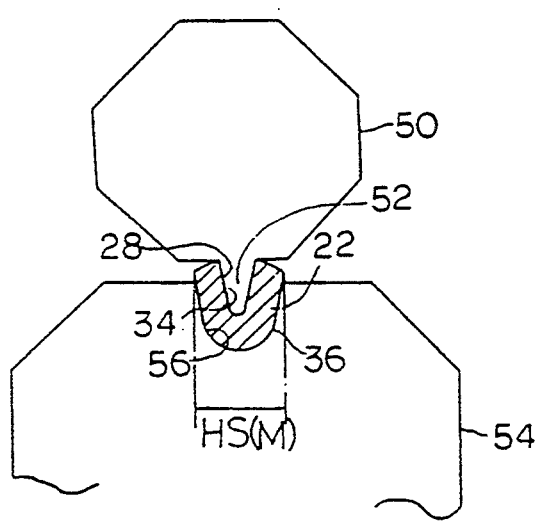
FIG. 5 is a cross-sectional view taken along line V—V of FIG. 3.
Figure 6:
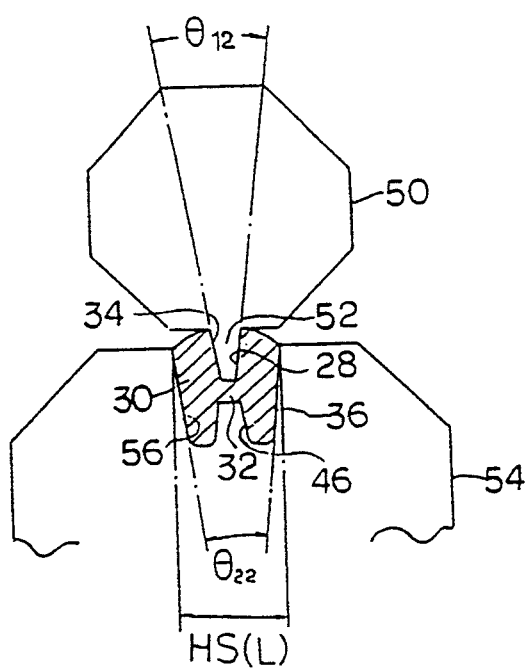
FIG. 6 is a cross-sectional view taken along line VI—VI of FIG. 3.

The needle blank 10 configured as shown in FIG. 1 is then subject to an operation such as swaging, plastic working such as rolling or the like, or grinding, resulting in the blank 10 being configured as shown n FIG. 2. More particularly, the operation permits the second blade section 16 to be formed at an intermediate portion thereof with an elongated portion 22 of a cylindrical shape and slant portions 24 and 26 respectively connected to both ends of the elongated portion 22. The elongated portion 22 is formed with a diameter smaller than that of the second blade section 16 and the slant portions 24 and 26 are each formed into a frust-conical shape and arranged so as to have the elongated portion 22 interposed therebetween. The elongated portion 22 and slant portions 24 and 26 are provided so as to positionally correspond to a clearance-above-eye formed in a blade of a finished sewing machine needle. The elongated portion 22 is preferably formed with a sectional area corresponding to 60 to 70% of that of the second blade section 16. More preferably, the sectional area of the elongated portion 22 is defined so as to correspond to 65% of that of the second blade section 16. A sectional area of the elongated portion 22 below 60% causes an excessive decrease in the sectional area of the clearance-above-eye of the sewing machine needle, so that the strength of the needle deteriorates, leading to breakage of the needle, whereas a sectional area above 70% fails to provide the clearance-above-eye with a depth required for sewing.

The needle blank 10 thus formed with the elongated portion 22 is then subject to a die press operation or die pressing, as shown in FIGS. 3 to 6, to thereby be formed with a continuous long groove 28 and an eye portion 30 including a thin eye accommodating web 32. More particularly, the die pressing results in the needle blank 10 being provided with the long groove 28 of a recessed shape in a manner to continuously extend from the shank 12 to a portion of the second blade section 16 in proximity to a distal end thereof. Also, the die pressing results in the second blade section 16 being formed with the eye portion 30 including the thin eye accommodating web 32 arranged along the long groove 28, as well as a clearance-above-eye 40 being formed in a manner to be positioned on a side of the second blade section 16 opposite to the long groove 28. The first blade section 14 and second blade section 16 including the elongated portion 22 which are commonly provided with the long groove 28 are formed into a substantially U- or V-shape in cross section, so that inner side surfaces 34 of the blade defining the long groove 28 and its outer surfaces 36 are each upwardly outward spread so as to be spaced from each other at a predetermined angle.

Figure 7:
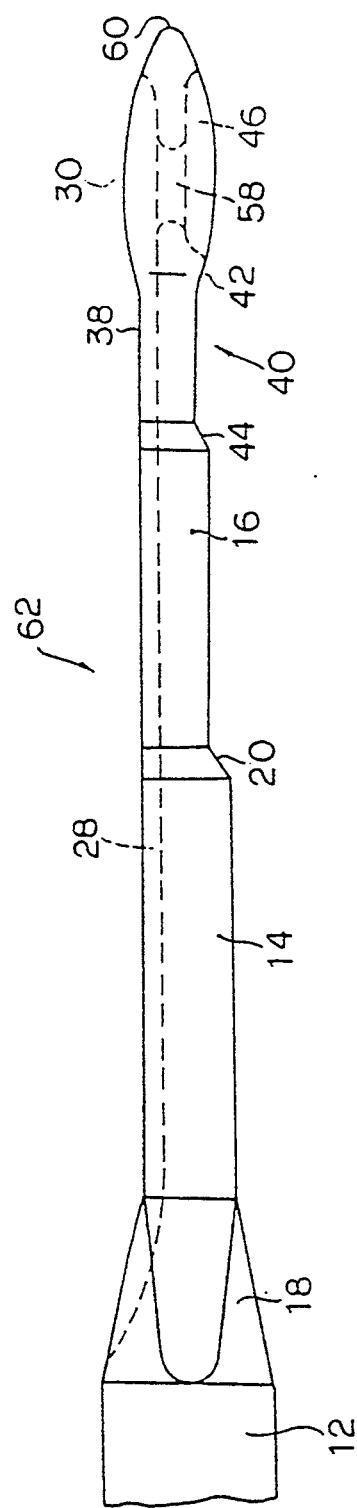
FIG. 7 is a fragmentary side elevation view showing an example of a sewing machine needle manufactured according to a method of the present invention.
Figure 8:
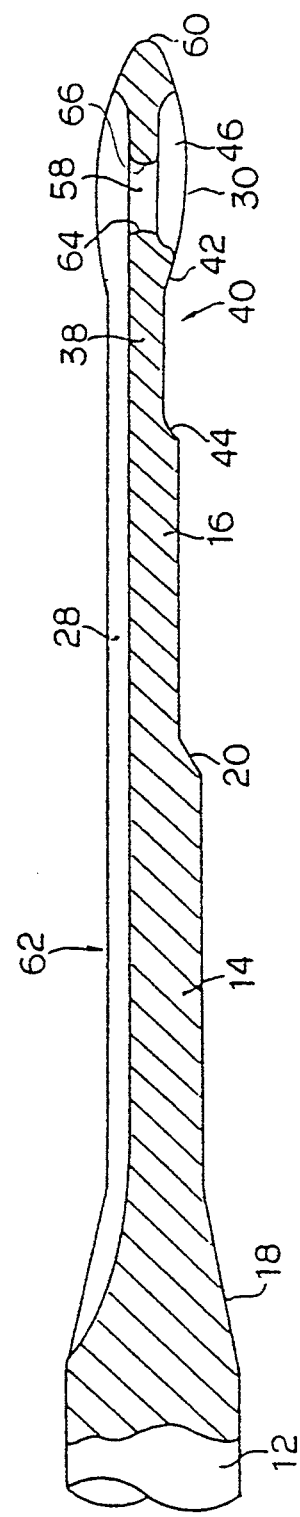
FIG. 8 is a longitudinal sectional view of the sewing machine needle shown in FIG. 7.
Figure 9:
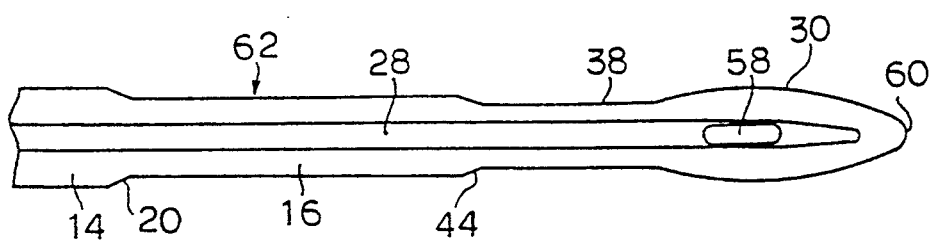
FIG. 9 is a fragmentary plan view showing a distal end of the sewing machine needle of FIG. 7.
Figure 10:
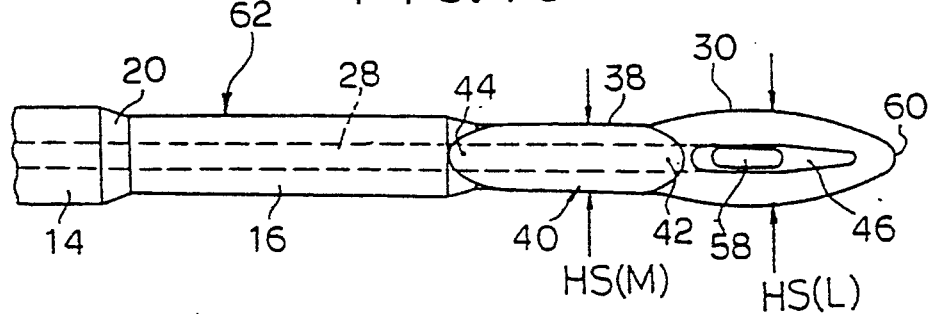
FIG. 10 is a fragmentary bottom view showing the distal end of the sewing machine needle of FIG. 7.

The U-shaped configuration of the first and second blade sections 14 and 16 is so defined that the size of the elongated portion 22 is smaller than that of the second blade section 16. The elongated portion 22 thus formed provides the finished sewing machine needle with a constriction 38 positioned above the eye portion 30 as shown in FIG. 7. More particularly, the elongated portion 22 is formed with the clearance-above-eye 40 in a manner to be recessed due to slant portions 42 and 44 formed so as to inwardly slant at a predetermined inclination angle with respect to an axis of the needle blank 10. The eye portion 30 is formed on a side thereof opposite to the long groove 28 with a short groove 46, which groove substantially extends from a portion thereof near the clearance-above-eye 40 to a needle point while forming the thin eye accommodating web 32 at which a needle eye is to be formed.

Further, the die pressing results in the needle blank 10 being formed with a laterally projecting flat portion 48 at a free end of the second blade section 16 beyond a portion of the second blade section 16 at which the needle point is to be formed. The flat portion 48 thus provided permits metal of which the needle blank 10 is made to readily flow during the die pressing and a predetermined positional relationship between the needle blank and dies for the die pressing in a longitudinal direction of the needle blank to be established. Also, provision of the flat portion 48 permits a die and a punch for punching an eye hole to be appropriately positioned to a degree sufficient to ensure accurate punching in a subsequent punching step.

The die pressing is carried out using an upper die 50 provided with a V-shaped projection 52 and a lower die 54 formed with a recess 56 corresponding to the projection 52. The first and second blade sections 14 and 16 are subject to deformation by being pressed between both dies 50 and 54, to thereby cause metal of which the blade sections are made to flow in a cavity between the dies to ensure satisfactory formation of the long groove 28 and eye portion 30 without producing any burr on the blade sections.

A space between the inner side surfaces 34 of each of the blade sections 14 and 16 defining the long groove 28 and a space between its outer side surfaces 36 are desirably upward spread at an angle of 10 to 28 degrees from the viewpoint of sewing and die pressing. For example, both outer side surfaces of the V-shaped projection 52 of the upper die 50 positionally corresponding to the first and second blade sections 14 and 16 are spread so as to be spaced from each other at an angle $\theta_{11}$ below 30 degrees and preferably 28 degrees, and an angle $\theta_{21}$ between of inner side surfaces of the recess 56 of the lower die 54 corresponding thereto is preferably set to be between 20 degrees and 28 degrees. The angle $\theta_{21}$ below 20 degrees makes it difficult for an excessive material of the blade blank to upward flow during the die pressing, so that a height of the blade sections 14 and 16 is decreased to cause the material to downward move with result that durability of the lower die 54 is reduced; whereas the angle $\theta_{21}$ above 28 degrees causes a width of the blade sections to be excessively increased. Thus, the angle $\theta_{21}$ is preferably set to be about 24 degrees, to thereby increase an area of a bottom surface of the die to prevent a width of an inlet of the long groove 28 from being excessively increased. An angle $\theta_{12}$ between outer surfaces of a portion of the V-shaped projection 52 of the upper die 50 in proximity to the eye portion 30 is set to be about 25 degrees and an angle $\theta_{22}$ between both inner side surfaces of the recess 56 of the lower die 54 corresponding thereto is defined to be between 10 degrees and 18 degrees and preferably about 14 degrees. The angle $\theta_{22}$ below 10 degrees causes a failure to remove the needle blank 10 from the dies during the die pressing, whereas the angle $\theta_{22}$ above 18 degrees causes a radius of a bottom of the recess 56 to be excessively small when the eye portion 30 is to be formed with a width in accordance with specifications, so that a bank for the short groove 46 is not satisfactorily formed. Thus, the angle $\theta_{22}$ between both side surfaces of the recess 56 of the lower die 54 is preferably set to be about 14 degrees, to thereby ensure that the needle blank 10 can be readily removed from the dies while being effectively prevented from adhering to the dies during the die pressing. Further, it will be noted that the angle between both side surfaces of the projection 52 of the upper die 50 is set to be in a range sufficient to facilitate threading of a sewing thread to increase a sewing speed and prevent a width of the needle blank from being excessively increased.

Formation of the clearance-above-eye 40 is carried out by using the elongated portion 22 previously formed in order to prevent the constriction portion 38 from laterally excessively expanding. As described above, the elongated portion 22 of the needle blank 10 is formed with an outer diameter sufficient to permit the constriction portion 38 at which the clearance-above-eye 40 is formed to have a sectional area which corresponds to about 65% of that of the second blade section 16. Also, the shape of each of the slant portions 24 and 26 arranged at both ends of the elongated portion 22 is conveniently defined on the basis of an inclination angle thereof rather than a length thereof in an axial direction thereof, because the needle blank 10 is extended in an axial direction thereof during the pressing. In the illustrated embodiment, it is preferable that an inclination angle $\alpha_1$ of the slant portion 24 arranged in proximity to the eye portion 30 be larger than an inclination angle $\alpha_2$ of the slant portion 26 arranged away from the eye portion 30. This is preferred because a portion of the metal of the needle blank in proximity to the eye portion is permitted to readily flow toward the long groove 28, resulting in the eye portion 30 being formed into a desired shape, when a distance between an upper end of the needle eye (defined based on the assumption that the sewing needle is mounted in a sewing machine) and the clearance-above-eye 40 is set as small as possible. In view of the above, the inclination angles $\alpha_1$ and $\alpha_2$ of the slant portions 24 and 26 are set to be, for example, about 18 degrees and about 13 degrees, respectively. These angles, when expressed on the basis of gradients of the slant portions 24 and 26 with respect to an axis of the needle blank, are about 9 degrees and about 6.5 degrees, respectively.

The dimensional relationships between the elongated portion 22 and slant portions 24 and 26 of the needle blank 10 prior to the die pressing and those of the finished sewing machine needle are conveniently determined as follows:

$$HL_1 = L_1 \times 0.6$$

$$HL_2 = L_2 \times 0.5$$

$$HL_3 = H - (HL_1 + HL_2) - 0.1$$

wherein $HL_1$, $HL_2$ and $HL_3$ are lengthwise dimensions of the slant portions 24 and 26 and elongated portion 22 of the needle blank 10 prior to the die pressing, respectively; $L_1$, $L_2$ and $L_3$ are lengthwise dimensions of the slant portions 42 and 44 of the finished sewing machine needle and a bottom of the clearance-above-eye 40 of the needle, respectively; and H is the whole length of the clearance-above-eye 40.

The needle blank 10 which has been thus subject to the die pressing is then subject to working to remove the thin eye accommodating web 32 to form a needle eye 58. Formation of the needle eye 58 is carried out by fitting the flat portion 48 formed at the distal end of the second blade section in a receiver formed on a punching die and fixing the needle blank 10 in the die while aligning the needle blank with the die to ensure accurate punching. Then, a distal end of the second blade section 16 is sharply machined to form a needle point 60, resulting in the formation of a sewing machine needle 62 being completed.

The sewing machine needle 62 thus completed, as shown in FIGS. 7 to 10, is formed at portion of the second blade section 16 positioned on the side of the shank 12 above the eye portion 30 with the constriction portion 38 of a width smaller than the eye portion 30. Also, the sewing machine needle 62 is formed with the clearance-above-eye 40 in a manner to be recessed due to the slant portions 42 and 44 formed so as to inward slant at a predetermined inclination angle with respect to the axis of the needle blank 10. This results in the portion of the second blade section 16 positioned on the side of the shank 12 above the eye portion 30 being inward deviated by the clearance-above-eye 40 so that an increased space between a sewing thread and the second blade section 16 is provided. An end of the needle eye 58 on the side of the shank 12 and that on the side of the needle point 60 are each formed into a convex-like curved shape, as respectively indicated at reference numerals 64 and 66.

A width HS(L) of a central portion of the needle eye 58 and a width HS(M) of a central portion of the constriction portion 38 may be suitably determined. For example, when the illustrated embodiment is applied to a sewing machine needle of Needle Size no. 7 defined in Japanese Industrial Standards (JIS), the widths HS(L) and. HS(M) may be 0.65 mm and 0.52 mm, respectively; whereas in Needle Size No. 9, HS(L) and HS(M) may be 0.75 mm and 0.62 mm, respectively. Also, in Needle Size No. 11, HS(L) and HS(M) may be 0.89 mm and 0.72 mm, respectively. The allowable dimensional deviation is set to within ±0.02 mm or ±0.03 mm Thus, in the sewing machine needle of the present invention, the blade is subject to double swaging and formed into a shape increased in height to prevent a width thereof from being increased, so that the whole needle may exhibit sufficient rigidity to eliminate breaking of the needle during sewing. Also, the needle is formed with the clearance-above-eye having a depth sufficient to significantly increase a gap between the blade and a sewing thread, resulting in sewing being carried out stably and at a high speed. Further, a surface of the sewing machine needle is smoothly finished by pressing and the needle is formed with the constriction, therefore, the needle of the present invention has improved in penetration resistance and generates less heat.

We claim:

1. A method for manufacturing a sewing machine needle, said needle including a shank, a blade arranged so as to extend from said shank and a needle point formed at a distal end of said blade, in which a continuous long groove of a recessed shape is provided so as to extend from said shank to a portion of said blade in proximity to said needle point, a needle eye portion is formed along said long groove and said blade is formed with a clearance-above-eye, comprising the steps of:

forming a needle blank with said shank of a large diameter and a cylindrical shape, a first blade section of a diameter smaller than said shank contiguous to a distal end of said shank and a second blade section of a diameter smaller than said first blade section contiguous to a distal end of said first blade section, said first and second blade sections constituting said blade;

forming said second blade section with an elongated portion corresponding to said clearance-above-eye of the sewing machine needle, the elongated portion having a smaller diameter than the remaining portion of the second blade section; and subjecting said blade to die pressing to form said long groove of a recessed shape extending from said shank to a portion of said second blade section in proximity to said needle point and said needle eye portion having a thin eye accommodating web arranged along said continuous groove, and deforming said elongated portion to form said clearance-above-eye;

said long groove of said blade having inner side surfaces and outer side surfaces spread at a predetermined angle, respectively, by deforming said blade.

2. A method as defined in claim 1, wherein said elongated portion is formed into a sectional area corresponding to about 60 to 70% of that of said second blade section.

3. A method as defined in claim 2, wherein said elongated portion is formed into a sectional area corresponding to about 65% of that of said second blade section.

4. A method as defined in claim 1, wherein said die pressing is carried out by using a pair of upper and lower dies which mate with each other;

said lower die for forming outer side surfaces of said blade being formed so as to have a blade holding angle between 20 degrees and 28 degrees and a blade holding angle of said lower die in proximity to said needle eye portion being set between 10 degrees and 18 degrees;

said upper die being provided with a projection having outer side surfaces for forming said inner side surfaces of said long groove, said outer side surfaces of said projection having an angle below 30 degrees set therebetween.

5. A method as defined in claim 4, wherein said blade holding angle of said lower die for forming said outer side surfaces of said blade is set at about 24 degrees and said holding angle of said lower die in proximity to said needle eye portion is set at about 14 degrees.

6. A method as defined in claim 4, wherein said angle between said outer side surfaces of said projection of said upper die for forming said inner side surfaces of said long groove is set at about 28 degrees and said angle between said outer surfaces in proximity to said needle eye portion is set at about 25 degrees.

7. A method as defined in claim 5, wherein said angle between said outer side surfaces of said projection of said upper die for forming said inner side surfaces of said long groove is set at about 28 degrees and said angle between said outer surfaces in proximity to said needle eye portion is set at about 25 degrees.

8. A method as defined in claim 2, wherein said elongated portion is formed at both ends thereof with slant portions slanting with respect to an axis of said needle through which said elongated portion is connected to said second blade section;

the slant portion arranged in proximity to said needle eye portion has an inclination angle larger than the other slant portion.

9. A method as defined in claim 4, wherein said elongated portion is formed at both ends thereof with slant portions slanting with respect to an axis of said needle through which said elongated portion is connected to said second blade section;

the slant portion arranged in proximity to said needle eye portion has an inclination angle larger than the other slant portion.

10. A method as defined in claim 8, wherein said slant portion arranged in proximity to said needle eye portion has an inclination angle set at about 9 degrees and the other slant portion has an inclination angle set at about 6.5 degrees.

11. A method as defined in claim 9, wherein said slant portion arranged in proximity to said needle eye portion has an inclination angle set at about 9 degrees and the other slant portion has an inclination angle set at about 6.5 degrees.

12. A sewing machine needle including a cylindrical shank of a large diameter, a blade arranged so as to extend from said shank and a sharp needle point formed at a distal end of said blade, in which a continuous long groove of a recessed shape is provided so as to extend from said shank to a portion of said blade in proximity to said needle point, a needle eye portion is formed along said long groove and said blade is formed with a clearance-above-eye;

wherein said blade is divided into a first blade section and a second blade section through a first and second frust-conical portion formed on said blade in a manner to be spaced from each other, said needle eye portion being arranged at said second blade section;

a constriction is arranged contiguous to said second blade section and spaced from the second frust-conical portion and in proximity to said needle eye portion of said second blade section and formed into a sectional area smaller than said second blade section;

a clearance-above-eye is provided on said constriction in a manner to be opposite to said long groove;

said blade has inner side surfaces defining said long groove and outer side surfaces, each being spread at a predetermined angle; and said constriction, clearance-above-eye, inner side surfaces and outer side surfaces are formed by die pressing.

13. A sewing machine needle as defined in claim 12, wherein said constriction is formed into a sectional area corresponding to about 60 to 70% of that of said second blade section.

14. A sewing machine needle as defined in claim 12, wherein said angle between said inner side surfaces is set below 30 degrees;

said angle between said outer side surfaces at said blade is set at an angle of 20 to 28 degrees; and said angle between said outer side surfaces of a portion of said blade in proximity to said needle eye portion is set at an angle of 10 to 18 degrees.

15. A sewing machine needle as defined in claim 14, wherein said angle between said outer side surfaces is about 24 degrees at said blade and about 14 degrees at said portion in proximity to said needle eye portion.

16. A sewing machine needle as defined in claim 14, wherein said angle between said inner side surfaces is about 28 degrees at said blade and about 25 degrees at said portion in proximity to said needle eye portion.

17. A sewing machine needle as defined in claim 12, wherein said clearance-above-eye is formed at both ends thereof with slant portions slanting with respect to an axis of the needle through which said clearance-above-eye is connected to said second blade section;

the slant portion arranged in proximity to said needle eye portion being formed into an inclination angle larger than that of the other slant portion.

18. A method as defined in claim 2, wherein said die pressing is carried out by using a pair of upper and lower dies which mate with each other;

said lower die for forming outer side surfaces of said blade being formed so as to have a blade holding angle between 20 degrees and 28 degrees and a blade holding angle of said lower die in proximity to said needle eye portion being set between 10 degrees and 18 degrees;

said upper die being provided with a projection having outer side surfaces for forming said inner side surfaces of said long groove, said outer side surfaces of said projection having an angle below 30 degrees set therebetween.

19. A sewing machine needle as defined in claim 13, wherein said angle between said inner side surfaces is set below 30 degrees;

said angle between said outer side surfaces at said blade is set at an angle of 20 to 28 degrees; and said angle between said outer side surfaces of a portion of said blade in proximity to said needle eye portion is set at an angle of 10 to 18 degrees.

20. A sewing machine needle as defined in claim 13, wherein said clearance-above-eye is formed at both ends thereof with slant portions slanting with respect to an axis of the needle through which said clearance-above-eye is connected to said second blade section;

the slant portion arranged in proximity to said needle eye portion is being formed into an inclination angle larger than that of the other slant portion.

* * * * *